(12) United States Patent
Hanson et al.

(10) Patent No.: US 8,519,132 B2
(45) Date of Patent: Aug. 27, 2013

(54) MILD AND SELECTIVE VANADIUM-CATALYZED OXIDATION OF BENZYLIC, ALLYLIC, AND PROPARGYLIC ALCOHOLS USING AIR

(75) Inventors: Susan Kloek Hanson, Los Alamos, NM (US); Louis A. Silks, Los Alamos, NM (US); Ruilian Wu, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 13/414,975

(22) Filed: Mar. 8, 2012

(65) Prior Publication Data
US 2012/0232279 A1 Sep. 13, 2012

Related U.S. Application Data

(60) Provisional application No. 61/450,502, filed on Mar. 8, 2011.

(51) Int. Cl.
*C07F 9/00* (2006.01)
*C07C 45/37* (2006.01)

(52) U.S. Cl.
USPC ............................................ 546/10; 568/320

(58) Field of Classification Search
USPC .......................................... 546/10; 568/320
See application file for complete search history.

(56) References Cited

PUBLICATIONS

Hanson, S. et al.: Mild and selective Vanadium-ctalyzed oxidation of benzylic, allylic, and propargylic alcohols using air. Org. Lett., vol. 13, pp. 1908-1911, 2011.*

* cited by examiner

*Primary Examiner* — Charanjit Aulakh
(74) *Attorney, Agent, or Firm* — Woodcock Washburn, LLP (57) ABSTRACT

The invention concerns processes for oxidizing an alcohol to produce a carbonyl compound. The processes comprise contacting the alcohol with (i) a gaseous mixture comprising oxygen; and (ii) an amine compound in the presence of a catalyst, having the formula:

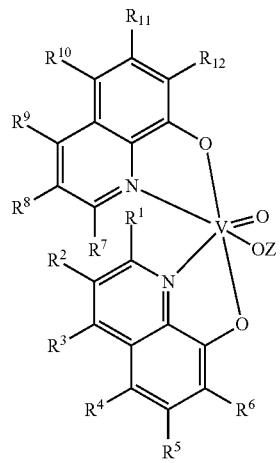

where each of $R^1$-$R^{12}$ are independently H, alkyl, aryl, $CF_3$, halogen, $OR^{13}$, $SO_3R^{14}$, $C(O)R^{15}$, $CONR^{16}R^{17}$ or $CO_2R^{18}$; each of $R^{13}$-$R^{18}$ is independently alkyl or aryl; and Z is alkl or aryl.

17 Claims, 2 Drawing Sheets

MILD AND SELECTIVE VANADIUM-CATALYZED OXIDATION OF BENZYLIC, ALLYLIC, AND PROPARGYLIC ALCOHOLS USING AIR

CROSS-REFERENCE TO RELATED APPLICATIONS

This application claims the benefit of U.S. Provisional Patent Application No. 61/450,502 entitled "Mild and Selective Vanadium-Catalyzed Oxidation of Benzylic, Allylic, and Propargylic Alcohols Using Air," filed Mar. 8, 2011, and is incorporated herein in its entirety by reference.

STATEMENT REGARDING FEDERAL RIGHTS

This invention was made with government support under Contract No. DE-AC52-06NA25396 awarded by the U.S. Department of Energy. The government has certain rights in the invention.

TECHNICAL FIELD

The present invention relates to the oxidation of alcohols in the presence of vanadium-containing catalyst.

BACKGROUND

The oxidation of alcohols to afford carbonyl compounds is a key reaction in synthetic organic chemistry. Recent years have seen major progress in the development of catalytic aerobic alcohol oxidation, which offers economic and environmental benefits over traditional stoichiometric oxidants (Schultz, M. J.; Sigman, M. S. *Tetrahedron* 2006, 62, 8227-8241; Punniyamurthy, T.; Velusamy, S.; Iqbal, J. *Chem. Rev.* 2005, 105, 2329-2363; Stahl, S. S. *Angew. Chem. Int. Ed.* 2004, 43, 3400-3420). Despite these advances, many reported catalysts include precious metals (Pd, Ru, Ir) and use oxygen pressures of 1 atm or more (Schultz, M. J.; Adler, R. S.; Zierkiewicz, W.; Privalov, T.; Sigman, M. S. *J. Am. Chem. Soc.* 2005, 127, 8499-8507; Steinhoff, B. A.; Guzei, I. A.; Stahl, S. S. *J. Am. Chem. Soc.* 2004, 126, 11268-11278; ten Brink, G. J.; Arends, I. W. C. E.; Sheldon, R. A. *Science* 2000, 287, 1636-1639; Nishimura, T.; Onoue, T.; Ohe, K.; Uemura, S. *J. Org. Chem.* 1999, 64, 6750-6755; Johnston, E. V.; Karlsson, E. A.; Tran, L. H.; Akermark, B.; Backvall, J. E. *Eur. J. Org. Chem.* 2010, 1971-1976; Nikaidou, F.; Ushiyama, H.; Yamaguchi, K.; Yamashita, K.; Mizuno, N. *J. Phys. Chem. C* 2010, 114, 10873-10880; Mizoguchi, H.; Uchida, T.; Ishida, K.; Katsuki, T. *Tetrahedron Lett.* 2009, 50, 3432-3435; Wolfson, A.; Wuyts, S.; De Vos, D. E.; Vankelecom, I. F. J.; Jacobs, P. A. *Tetrahedron Lett.* 2002, 43, 8107-8110; Arita, S.; Koike, T.; Kayaki, Y.; Ikariya, T. *Angew. Chem. Int. Ed.* 2008, 47, 2447-2449; Jiang, B.; Feng, Y.; Ison, E. A. *J. Am. Chem. Soc.* 2008, 130, 14462-14464; Gabrielsson, A.; van Leeuwen, P.; Kaim, W. *Chem. Commun.* 2006, 4926-4927). There is considerable interest in replacing precious metal-containing catalysts with base metal-containing catalysts because base metals are less expensive and more abundant that precious metals (Michel, C.; Belanzoni, P.; Gamez, P.; Reedijk, J.; Baerends, E. J. *Inorg. Chem.* 2009, 48, 11909-11920; Jiang, N.; Ragauskas, A. J. *J. Org. Chem.* 2006, 71, 7087-7090; Gamez, P.; Arends, I. W. C. E.; Sheldon, R. A.; Reedijk, J. *Adv. Synth. Catal.* 2004, 346, 805-811; Gamez, P.; Arends, I. W. C. E.; Reedijk, J.; Sheldon, R. A. *Chem. Commun.* 2003, 2414-2415; Chaudhuri, P.; Hess, M.; Florke, U.; Wieghardt, K. *Angew. Chem. Int. Ed.* 1998, 37, 2217-2220; Marko, I. E.; Giles, P. R.; Tsukazaki, M.; Brown, S. M.; Urch, C. J. *Science* 1996, 274, 2044-2046). Using air instead of pure oxygen ($O_2$) is also advantageous (for selected examples of aerobic oxidation using air see: (a) Zahmakiran, M.; Akbayrak, S.; Kodaira, T.; Ozkar, S. *Dalton Trans.* 2010, 39, 7521-7527; Bailie, D. S.; Clendenning, G. M. A.; McNamee, L.; Muldoon, M. J. *Chem. Commun.* 2010, 46, 7238-7240; Conley, N. R.; Labios, L. A.; Pearson, D. M.; McCrory, C. C. L.; Waymouth, R. M. *Organometallics* 2007, 26, 5447-5453; Guan, B.; Xing, D.; Cai, G.; Wan, X.; Yu, N.; Fang, Z.; Yang, L.; Shi, Z. *J. Am. Chem. Soc.* 2005, 127, 18004-18005; Iwasawa, T.; Tokunaga, M.; Obora, Y.; Tsuji, Y. *J. Am. Chem. Soc.* 2004, 126, 6554-6555; Korovchenko, P.; Donze, C.; Gallezot, P.; Besson, M. *Catal. Today* 2007, 121, 13-21; Hara, T.; Ishikawa, M.; Sawada, J.; Ichikuni, N.; Shimazu, S. *Green Chem.* 2009, 11, 2034-2040), reducing the safety hazard associated with heating organic solvents under elevated $O_2$ pressures.

Vanadium complexes have shown potential as base-metal catalysts for aerobic alcohol oxidation, in some cases proving effective for substrates where palladium catalysts display limited activity. For instance, vanadium is known to catalyze the selective aerobic oxidation of propargylic alcohols, a reaction using $V^{IV}(O)(acac)_2$ (1-5 mol %) and molecular sieves at 80° C. (Maeda, Y.; Kakiuchi, N.; Matsumura, S.; Nishimura, T.; Kawamura, T.; Uemura, S. *J. Org. Chem.* 2002, 67, 6718-6724; Maeda, Y.; Kakiuchi, N.; Matsumura, S.; Nishimura, T.; Uemura, S. *Tetrahedron Lett.* 2001, 42, 8877-8879). The combination of $V^{IV}(O)(acac)_2$ and DABCO (DABCO=1,4-diazabicyclo[2.2.2]octane) also catalyzes the oxidation of benzylic and allylic alcohols in ionic liquid solvent at 80-100° C. (Jiang, N.; Ragauskas, A. J. *Tetrahedron Lett.* 2007, 48, 273-276; Jiang, N.; Ragauskas, A. J. *J. Org. Chem.* 2007, 72, 7030-7033). Vanadium catalysts with chiral Schiff-base ligands effect the oxidative kinetic resolution of α-hydroxyesters, amides, and phosphonates (Radosevich, A. T.; Musich, C.; Toste, F. D. *J. Am. Chem. Soc.* 2005, 127, 1090-1091; Pawar, V. D.; Bettigeri, S.; Weng, S. S.; Kao, J. Q.; Chen, C. T. *J. Am. Chem. Soc.* 2006, 128, 6308-6309; Weng, S. S.; Shen, M. W.; Kao, J. Q.; Munot, Y. S.; Chen, C. T. *Proc. Nat. Acad. Sci.* 2006, 103, 3522-3527). These reports are promising indications of the versatility of vanadium catalysts, but each requires an atmosphere of pure oxygen. Very recently, Ohde and Limberg reported a metavanadate-cinnamic acid catalyst that catalyzes the oxidation of activated alcohols using mixtures of argon and $O_2$, but this catalyst is highly moisture sensitive (Ohde, C.; Limberg, C. *Chem. Eur. J.* 2010, 16, 6892-6899).

There is a need in the art for an oxidation process that utilizes a robust base metal catalyst which can oxidize alcohols in the presence of air.

SUMMARY

The present invention provides processes for oxidizing an alcohol to produce a carbonyl compound, the process comprising contacting the alcohol with (i) a gaseous mixture comprising oxygen; and (ii) an amine compound;

the contacting occurring in the presence of a catalyst comprising two nitrogen-containing heterocycles complexed with vanadium and having the formula:

where each of $R^1$-$R^{12}$ are independently H, alkyl, aryl, $CF_3$, halogen, $OR^{13}$, $SO_3R^{14}$, $C(O)R^{15}$, $CONR^{16}R^{17}$ or $CO_2R^{18}$; each of $R^{13}$-$R^{18}$ is independently alkyl or aryl; and Z is alkl or aryl. In some embodiments, the contacting is performed in a gaseous mixture comprising from 5 to about 35 molar percent oxygen.

In some embodiments, Z is alkyl. In one preferred embodiment, Z is isopropyl. Some amines useful in the inventive reaction are trialkyl amines. Preferred amines include triethylamine, diisopropylethylamine, 1,4-diazabicyclo[2.2.2]octane, or 2,2,6,6-tetramethylpiperidine-1-oxyl. One preferred amine is triethylamine.

Some catalysts are of a formula where each of $R^1$-$R^{12}$ is H, alkyl or aryl. In one preferred embodiment, each of $R^1$-$R^{12}$ is H.

While the invention is applicable to numerous alcohols, some preferred alcohols are of the formula:

where $R^{19}$ is selected from aryl, vinyl, and alkynyl, and $R^{20}$ is selected from H, methyl, and aryl. In some preferred embodiments, the alcohol is a benzylic alcohol, allylic alcohol, or propargylic alcohol.

The process of the invention may be run with or without the presence of a solvent. In some preferred embodiments, the contacting of the reactants and catalyst occurs in the presence of a solvent selected from one or more of water, 1,2-dichloroethane, ethylacetate, toluene, tetrahydrofuran, acetonitrile, dichloromethane, 1,2-dichlorobenzene and 2-methyl-tetrahydrofuran.

In some embodiments, the contacting occurs at a temperature in the range of from ambient temperature (e.g., 25° C. to 150° C.). In other embodiments, the temperature is in the range of from 40° C. to 80° C. or 40° C. to 75° C. or 50° C. to 70° C. In certain embodiments, the gaseous mixture is air. In other embodiments, the gaseous mixture is a mixture of inert gas (such as nitrogen or argon) and oxygen.

In one preferred embodiment, the catalyst is of the formula

DETAILED DESCRIPTION OF ILLUSTRATIVE EMBODIMENTS

Figure 1:
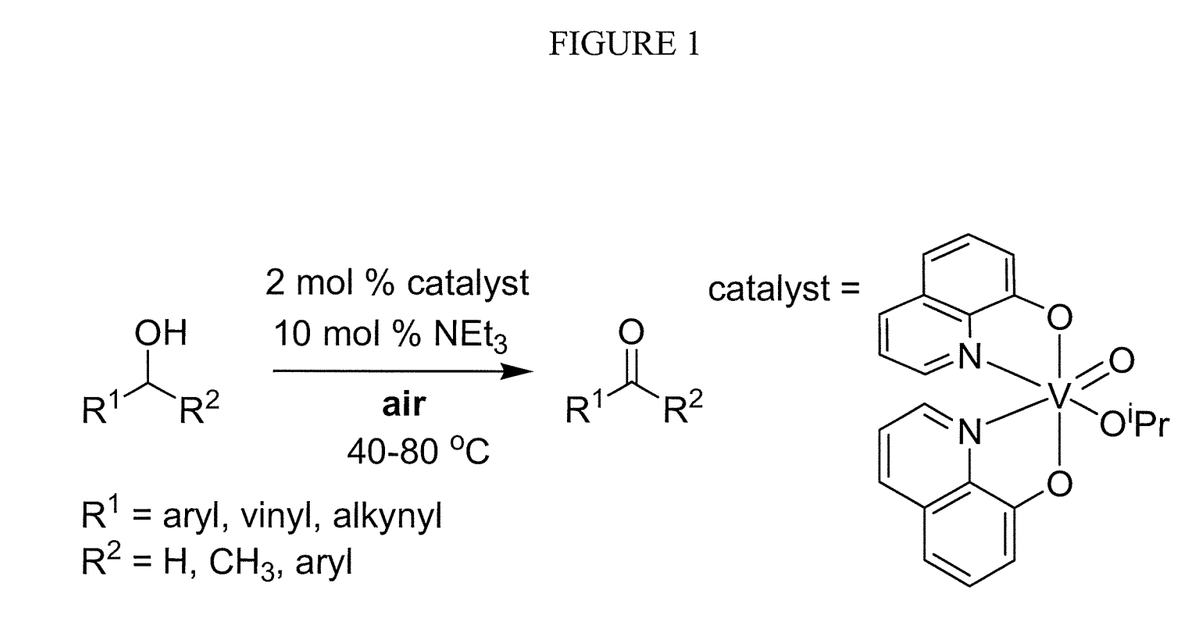
FIG. 1 shows a schematic of an oxidation reaction.

The present invention is concerned with a vanadium-based catalyst for the aerobic oxidation of benzylic, allylic, and propargylic alcohols. See, for example, FIG. 1. The oxidation reactions proceed under mild conditions (air, 40-80° C.), and in a variety of solvents. Moreover, the catalyst can be prepared in air using commercially available reagents, making the overall process inexpensive, simple, and accessible without requiring the use of a drybox or Schlenk techniques.

Figure 2:
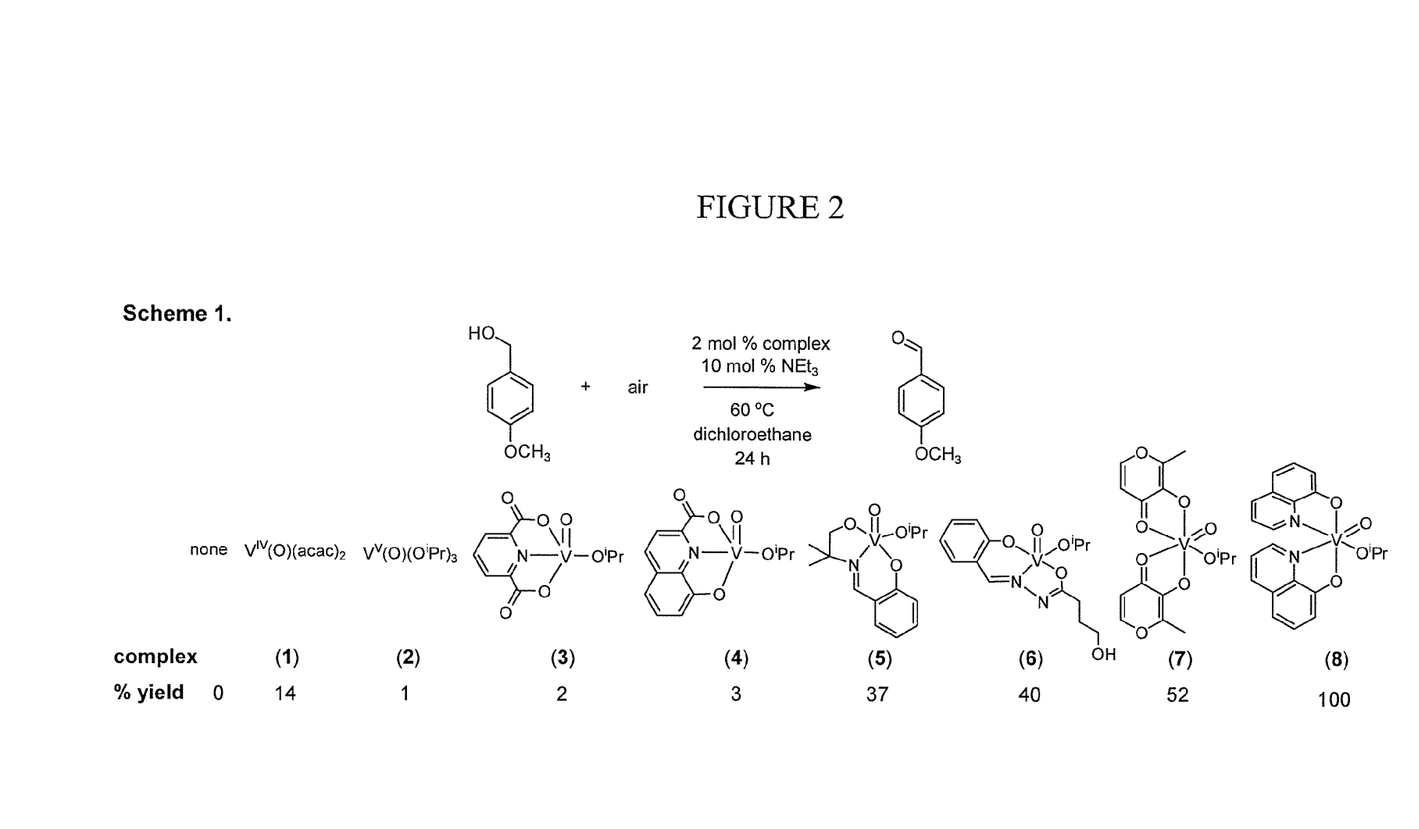
FIG. 2 (Scheme 1) shows results for the oxidation of 4-methoxybenzylalcohol with a variety of catalysts.

We recently studied the mechanism of alcohol oxidation by dipicolinate vanadium(V) complexes, and found that the base known as pyridine promoted alcohol oxidation (Hanson, S. K.; Baker, R. T.; Gordon, J. C.; Scott, B. L.; Silks, L. A.; Thorn, D. L. *J. Am. Chem. Soc.* 2010, 132, 17804-17816). Inspired by this finding, we tested the aerobic oxidation of 4-methoxybenzyl alcohol at 60° C. under air using several different vanadium complexes (2 mol %) and a base promoter (10 mol % $NEt_3$) in 1,2-dichloroethane (Scheme 1, FIG. 2). Poor yields were observed with $V^{IV}(O)(acac)_2$, $V^V(O)(O^iPr)_3$, and complexes of carboxylate-based ligands (dipicolinate (3) and 8-quinolinate-2-carboxylate (4)). Complexes with more electron-donating ligands displayed higher activity (Thorn, D. L.; Harlow, R. L.; Herron, N. *Inorg. Chem.* 1996, 35, 547-548; Nica, S.; Pohlmann, A.; Plass, W. *Eur. J. Inorg. Chem.* 2005, 2032-2036; Caravan, P.; Gelmini, L.; Glover, N.; Herring, F. G.; Li, H.; McNeill, J. H.; Rettig, S. J.; Setyawati, I. A.; Shuter, E.; Sun, Y.; Tracey, A. S.; Yuen, V. G.; Orvig, C. *J. Am. Chem. Soc.* 1995, 117, 12759-12770; Sun, Y.; James, B. R.; Rettig, S. J.; Orvig, C. *Inorg. Chem.* 1996, 35, 1667-1673), with the highest activity observed for the complex $(HQ)_2V^V(O)(O^iPr)$ (8) (HQ=8-quinolinate) reported by Sawyer, Floriani, and Scheidt (Scheme 1) (Scheidt, W. R. *Inorg. Chem.* 1973, 12, 1758-1761; Giacomelli, A.; Floriani, C.; Duarte, A. O. D. S.; Chiesi-Villa, A.; Guastini, C. *Inorg. Chem.* 1982, 21, 3310-3316; (b) Pasquali, M.; Landi, A.; Floriani, C. *Inorg. Chem.* 1979, 18, 2397-2400.; Riechel, T. L.; Sawyer, D. T. *Inorg. Chem.* 1975, 14, 1869-1875; (b) Amos, L. W.; Sawyer, D. T. *Inorg. Chem.* 1974, 13, 78-83). Complex 8 is easily prepared in one step by the reaction of 8-hydroxyquinoline with $V^{IV}(O)(acac)_2$ under air in isopropanol (see the examples below).

TABLE 1

Solvents tested for the oxidation of 4-methoxybenzylalcohol

| Entry | Solvent | % yield (NMR) |
|---|---|---|
| 1 | 1,2-dichloroethane | 99 |
| 2 | Ethyl acetate | 91 (99) |
| 3 | toluene | 78 (96) |
| 4 | Tetrahydrofuran (THF) | 96 (99) |
| 5 | Acetonitrile ($CH_3CN$) | 93 (98) |
| 6 | Dichloromethane ($CH_2Cl_2$) | $92^a$ ($99^a$) |
| 7 | 1,2-dichlorobenzene | 99 |
| 8 | 2-methyl-THF | 99 |
| 9 | Dimethylsulfoxide (DMSO) | 69 |
| 10 | pyridine | 12 |

Conditions: 2 mol % 8, 10 mol % triethylamine ($NEt_3$), 60 C., 24 hours.
Conditions for dichloromethane: 5 mol % 8, 40 C.
Values in parenthesis indicate percent yield after 48 hours reaction time.

Use of several different solvents for the oxidation of 4-methoxybenzylalcohol using 8 (2 mol %) and $NEt_3$ (10 mol %) were screened. High yields of the aldehyde were observed after 24 h at 60° C. in THF, ethyl acetate, and acetonitrile, with >99% NMR yield observed in 1,2-dichloroethane, 1,2-dichlorobenzene, and 2-methyltetrahydrofuran (Table 1, Entries 1 to 8).

The effect of the additive was then examined for the oxidation of 4-methoxybenzylalcohol using 8 (2 mol %) in 1,2-dichloroethane (Table 2). Triethylamine, diisopropylethylamine, and TEMPO were all effective promoters of the vanadium complex, affording high yields of 4-methoxybenzaldehyde after 24 h at 60° C. (Entries 2 to 5). In contrast, less than 5% yield was observed with the vanadium complex alone (no additive, Entry 1), suggesting a key role for the nitrogen base.

TABLE 2 additives tested for the oxidation of 4-methoxybenzyl alcohol

| entry | additive | % yield (NMR) |
|---|---|---|
| 1 | none | 4 |
| 2 | triethylamine | 99 (49) |
| 3 | Triethylamine (5 mol %) | 99 (42) |
| 4 | diisopropylethylamine | 99 (31) |
| 5 | TEMPO | 99 (8) |
| 6 | DABCO | 83 |
| 7 | DMAP | 28 |
| 8 | NaO$^t$Bu | 19 |
| 9 | $Na_2CO_3$ | 16 |
| 10 | DBU | 5 |
| 11 | Proton sponge | 6 |
| 12 | NaOAc | 1 |

Conditions: 2 mol % 8, 10 mol % additive, 1,2-dichloroethane solvent, 60° C., 24 hours.
Values in parenthesis indicate yields after 4 hours.

The substrate scope of the alcohol oxidation was investigated, using 8 (2 mol %) and $NEt_3$ (10 mol %) in 1,2-dichloroethane (Table 3). A range of benzylic alcohols were oxidized and the aldehydes or ketones isolated in high yields (Entries 1 to 8). Steric bulk around the alcohol slowed the reaction, with the more hindered α-isopropyl- and α-tert-butyl benzyl alcohols showing only 20 and 0% yield, respectively (Entries 7 and 8). Cinnamyl alcohol, 3-methyl-2-cyclohexen-1-ol, 5-hydroxy-methylfurfural (HMF), and 2-hydroxymethylpyridine were oxidized to the corresponding aldehyde or ketone in high yields (Entries 9 to 12).

2-Allyloxybenzylalcohol has been used by Galli and coworkers as a substrate probe in catalytic oxidations to detect the intermediate formation of a carbon-based radical, which has been reported to undergo an intramolecular ring closure as shown in Scheme 2 (Astolfi, P.; Brandi, P.; Galli, C.; Gentili, P.; Gerini, M. F.; Greci, L.; Lanzalunga, O, New J. Chem. 2005, 29, 1308-1317; Minisci, F.; Recupero, F.; Cecchetto, A.; Gambarotti, C.; Punta, C.; Faletti, R.; Paganelli, R.; Pedulli, G. F. Eur. J. Org. Chem. 2004, 109-119; and Bentley, J.; Nilsson, P. A.; Parsons, A. F. J. Chem. Soc., Perkin Trans 1, 2002, 1461-1469). This substrate was oxidized to the corresponding aldehyde in 95% isolated yield (Entry 13); none of ring-closed product A (Scheme 2) was detected by $^1H$ NMR (Astolfi, P.; Brandi, P.; Galli, C.; Gentili, P.; Gerini, M. F.; Greci, L.; Lanzalunga, O, New J. Chem. 2005, 29, 1308-1317; and Minisci, F.; Recupero, F.; Cecchetto, A.; Gambarotti, C.; Punta, C.; Faletti, R.; Paganelli, R.; Pedulli, G. F. Eur. J. Org. Chem. 2004, 109-119).

Scheme 2.

The secondary propargylic alcohol 4-phenyl-3-butyn-2-ol was also oxidized in high yield (96%, Entry 14). Primary propargylic alcohols 3-phenyl-2-propyn-1-ol and 2-decyn-1-ol were oxidized to the corresponding aldehydes in good yields (80% and 60% $^1H$ NMR yields, Entries 15 and 16, respectively). Oxidation of the terminal alkyne 1-phenyl-2-propyn-1-ol was less selective, affording the ketone product in only 38% yield ($^1H$ NMR, Entry 17) at complete conversion.

Simple aliphatic alcohols such as 1-butanol and 2-butanol underwent little or no oxidation, even when heated at 100° C. (Entries 18 and 19). This observed selectivity for activated alcohols was confirmed by oxidation of a mixture of 4-methoxybenzylic alcohol (5 mmol) and 1-octanol (5 mmol), which resulted in complete oxidation of the benzylic alcohol with no formation of 1-octanal.

For several of the benzylic alcohols, the oxidation proceeded selectively with no solvent (neat) using 8 (2 mol %) and $NEt_3$ (10 mol %) for 24 h at 100° C. However, lower selectivities were observed for the oxidations of cinnamyl alcohol, 5-hydroxymethylfurfural, and 4-phenyl-3-butyn-2-ol when no solvent was used.

To gain insight into the role of the base additive, $(HQ)_2V^V(O)(OC_6H_4OCH_3)$ (9) was prepared from the reaction of 8 with 4-methoxybenzylalcohol in acetonitrile. In the absence of base, complex 9 was relatively stable in $CD_2Cl_2$ solution, with less than 5% reacting after 16 h at room temperature. However, a rapid reaction occurred when a $CD_2Cl_2$ solution of 9 was treated with $NEt_3$ (2 equiv) under argon, affording the vanadium(IV) complex $(HQ)_2V^{IV}(O)$ (10), 4-methoxybenzaldehyde (0.5 equiv, 100% yield) and 4-methoxybenzylalcohol (0.5 equiv, 100% yield) within 2 h at room temperature (Scheme 3). The increased reactivity observed in the presence of $NEt_3$ suggests a key role for the base additive in promoting the alcohol oxidation step. When the reaction of 9 with $NEt_3$ was carried out under air in $CD_2Cl_2$, quantitative conversion to the cis-dioxo vanadium(V) complex $(HQ)_2V^V(O)_2HNEt_3$ (11) and 4-methoxybenzaldehyde was observed after 22 h at room temperature. Complex 11 was independently prepared by the reaction of the μ-oxo complex $[(HQ)_2V^V(O)]_2\mu\text{-}O$ (12) (Giacomelli, A.; Floriani, C.; Duarte, A. O. D. S.; Chiesi-Villa, A.; Guastini, C. *Inorg. Chem.* 1982, 21, 3310-3316) with $H_2O$ and $NEt_3$ in $CH_2Cl_2$. When tested for the oxidation of 4-methoxybenzylalcohol in combination with 10 mol % $NEt_3$, both complexes 10 and 11 were effective catalysts, affording complete conversion in 24 h at 60° C.

TABLE 3

Catalytic oxidation results.

| entry | substrate | product | % yield |
|---|---|---|---|
| 1 | HO-CHR-C6H4-X | O=CR-C6H4-X R=H X=H | 92 |
| 2 | | = OCH3 | 96 |
| 3 | | = NO2 | 96 |
| 4 | | X=H R=Ph | 93[d] |
| 5 | | = CH3 | 95[a,f] |
| 6 | | = cyclopropyl | 90[a,c] |
| 7 | | = iPr | (20)[a,d] |
| 8 | | = tBu | 0[a,d] |
| 9 | cinnamyl alcohol | cinnamaldehyde | 98 |
| 10 | 3-methylcyclohex-2-enol | 3-methylcyclohex-2-enone | 96[a] |
| 11 | 2-pyridylmethanol | 2-pyridinecarboxaldehyde | 98[a] |
| 12 | 5-(hydroxymethyl)furfural | 2,5-furandicarboxaldehyde | 94 |
| 13 | 2-(allyloxy)benzyl alcohol | 2-(allyloxy)benzaldehyde | 95 |
| 14 | 4-phenyl-3-butyn-2-ol | 4-phenyl-3-butyn-2-one | 96[a] |
| 15 | 3-phenyl-2-propyn-1-ol | 3-phenyl-2-propynal | (80) |
| 16 | oct-2-yn-1-ol (C5 chain) | oct-2-ynal | (60) |
| 17 | 1-phenyl-2-propyn-1-ol | 1-phenyl-2-propyn-1-one | (38) |
| 18 | 2-butanol | 2-butanone | (5)[b] |
| 19 | 1-butanol | butyraldehyde | (1)[b] |

Conditions:
2 mol % 8, 10 mol % $NEt_3$, 1,2-dichloroethane solvents, 60° C., 24 h.

[a]80° C.;

[b]100° C., dichlorobenzene solvent;

[c]48 h;

[d]72 h;

[f]= 1 equivalent $NEt_3$.

Values in parenthesis indicate NMR yield.

Initial experiments suggest that mass transport of oxygen may be a rate-limiting factor in the oxidation of 4-methoxybenzyl alcohol (Steinhoff, B. A.; Stahl, S. S. *J. Am. Chem. Soc.* 2006, 128, 4348-4355). When the oxidation was carried out in two different reaction vessels under otherwise identical conditions and stopped at an intermediate reaction time (4 h) (Conditions: 2 mol % 8, 10 mol % NEt₃, 1,2-dichloroethane solvent, 60° C.), the shape of the reaction vessel affected the extent of conversion. In a wide 100 mL round bottom flask, 55% conversion was observed after 4 h, while in a narrow 10 mL reaction tube, only 31% conversion occurred. The stir rate also affected the extent of conversion in two identical reactions conducted in 25 mL round bottom flasks.

In 1,2-dichloroethane, the catalytic oxidation of 4-methoxy-benzylalcohol was not found to be significantly affected by added water. When excess water (5 equiv, 5 mmol) was added to the oxidation of 4-methoxybenzylalcohol (1 mmol), >98% conversion to the aldehyde was observed after 24 h at 60° C. This tolerance of water allows the catalytic reaction to be carried out in the absence of drying agent, in contrast to several other reported vanadium catalysts which require the addition of molecular sieves (Maeda, Y.; Kakiuchi, N.; Matsumura, S.; Nishimura, T.; Kawamura, T.; Uemura, S. *J. Org. Chem.* 2002, 67, 6718-6724; Maeda, Y.; Kakiuchi, N.; Matsumura, S.; Nishimura, T.; Uemura, S. *Tetrahedron Lett.* 2001, 42, 8877-8879; and Ohde, C.; Limberg, C. *Chem. Eur. J.* 2010, 16, 6892-6899).

DEFINITIONS

As used herein, the term "alkyl" includes both branched and straight-chain saturated aliphatic hydrocarbon groups having the specified number of carbon atoms, e.g. methyl (Me), ethyl (Et), propyl (Pr), isopropyl (i-Pr), isobutyl (i-Bu), secbutyl (s-Bu), tertbutyl (t-Bu), isopentyl, isohexyl and the like. The term "alkyl" further includes both unsubstituted and mono-, di- and tri-substituted hydrocarbon groups, with halogen substitution particularly preferred in some preferred embodiments. In certain embodiments, preferred alkyl groups have 1 to 6 carbon atoms. In some preferred embodiments, alkyl groups have 1 to 4 carbon atoms. In yet other preferred embodiments, alkyl groups have 1 to 3 carbon atoms.

The term "aryl" means an aromatic carbocyclic moiety of up to 20 carbon atoms (e.g., 5-20), which may be a single ring (monocyclic) or multiple rings (bicyclic, up to three rings) fused together or linked covalently. Any suitable ring position of the aryl moiety may be covalently linked to the defined chemical structure. Some preferred aryl groups have 5 to 20 carbon atoms. Examples of aryl moieties include, but are not limited to, chemical groups such as phenyl, 1-naphthyl, 2-naphthyl, dihydronaphthyl, tetrahydronaphthyl, biphenyl. anthryl, phenanthryl, fluorenyl, indanyl, biphenylenyl, acenaphthenyl, acenaphthylenyl, and the like.

The term "halo" includes fluoro, chloro, iodo, and bromo.

The term "amine" includes aliphatic and aromatic amines. Amines include trialkyl amines, triaryl amines and amines containing both alkyl and aryl groups. Some preferred amines include triethylamine, diisopropylethylamine, 1,4-diazabicyclo[2.2.2]octane, and 2,2,6,6-tetramethylpiperidine-1-oxyl.

"Alcohol compound" refers to a compound that includes at least one alcohol group. Some preferred alcohols include benzylic alcohol, allylic alcohol, and propargylic alcohol. Other preferred alcohol compounds include lignin and lignocellulose, two biomass compositions that can be used, for among other things, to produce fuel products.

"Carbonyl compound" refers to a compound that includes at least one carbonyl group. Some preferred carbonyl compounds are the oxidation products of alcohol compounds discussed in the previous paragraph.

Articles indicating inclusion of "Teflon" refer to DuPont's trademarked fluoropolymer product. Other fluoropolymers may be used in connection with the inventive process.

REFERENCES

The following references are incorporated by reference herein.

Schultz, M. J.; Sigman, M. S. *Tetrahedron* 2006, 62, 8227-8241;
Punniyamurthy, T.; Velusamy, S.; Iqbal, J. *Chem. Rev.* 2005, 105, 2329-2363; (c) Stahl,
S. S. *Angew. Chem. Int. Ed.* 2004, 43, 3400-3420;
Schultz, M. J.; Adler, R. S.; Zierkiewicz, W.; Privalov, T.; Sigman, M. S. *J. Am. Chem. Soc.* 2005, 127, 8499-8507;
Steinhoff, B. A.; Guzei, I. A.; Stahl, S. S. *J. Am. Chem. Soc.* 2004, 126, 11268-11278;
ten Brink, G. J.; Arends, I. W. C. E.; Sheldon, R. A. *Science* 2000, 287, 1636-1639;
Nishimura, T.; Onoue, T.; Ohe, K.; Uemura, S. *J. Org. Chem.* 1999, 64, 6750-6755;
Johnston, E. V.; Karlsson, E. A.; Tran, L. H.; Akermark, B.; Backvall, J. E. *Eur. J. Org. Chem.* 2010, 1971-1976;
Nikaidou, F.; Ushiyama, H.; Yamaguchi, K.; Yamashita, K.; Mizuno, N. *J. Phys. Chem. C* 2010, 114, 10873-10880;
Mizoguchi, H.; Uchida, T.; Ishida, K.; Katsuki, T. *Tetrahedron Lett.* 2009, 50, 3432-3435;
Wolfson, A.; Wuyts, S.; De Vos, D. E.; Vankelecom, I. F. J.; Jacobs, P. A. *Tetrahedron Lett.* 2002, 43, 8107-8110;
Arita, S.; Koike, T.; Kayaki, Y.; Ikariya, T. *Angew. Chem. Int. Ed.* 2008, 47, 2447-2449;
Jiang, B.; Feng, Y.; Ison, E. A. *J. Am. Chem. Soc.* 2008, 130, 14462-14464;
Gabrielsson, A.; van Leeuwen, P.; Kaim, W. *Chem. Commun.* 2006, 4926-4927;
Michel, C.; Belanzoni, P.; Gamez, P.; Reedijk, J.; Baerends, E. J. *Inorg. Chem.* 2009, 48, 11909-11920;
Jiang, N.; Ragauskas, A. J. *J. Org. Chem.* 2006, 71, 7087-7090;
Gamez, P.; Arends, I. W. C. E.; Sheldon, R. A.; Reedijk, J. *Adv. Synth. Catal.* 2004, 346, 805-811;
Gamez, P.; Arends, I. W. C. E.; Reedijk, J.; Sheldon, R. A. *Chem. Commun.* 2003, 2414-2415;
Chaudhuri, P.; Hess, M.; Florke, U.; Wieghardt, K. *Angew. Chem. Int. Ed.* 1998, 37, 2217-2220;
Marko, I. E.; Giles, P. R.; Tsukazaki, M.; Brown, S. M.; Urch, C. J. *Science* 1996, 274, 2044-2046;
Zahmakiran, M.; Akbayrak, S.; Kodaira, T.; Ozkar, S. *Dalton Trans.* 2010, 39, 7521-7527;
Bailie, D. S.; Clendenning, G. M. A.; McNamee, L.; Muldoon, M. J. *Chem. Commun.* 2010, 46, 7238-7240;

Conley, N. R.; Labios, L. A.; Pearson, D. M.; McCrory, C. C. L.; Waymouth, R. M. *Organometallics* 2007, 26, 5447-5453;

Guan, B.; Xing, D.; Cai, G.; Wan, X.; Yu, N.; Fang, Z.; Yang, L.; Shi, Z. *J. Am. Chem. Soc.* 2005, 127, 18004-18005;

Iwasawa, T.; Tokunaga, M.; Obora, Y.; Tsuji, Y. *J. Am. Chem. Soc.* 2004, 126, 6554-6555;

Korovchenko, P.; Donze, C.; Gallezot, P.; Besson, M. *Catal. Today* 2007, 121, 13-21;

Hara, T.; Ishikawa, M.; Sawada, J.; Ichikuni, N.; Shimazu, S. *Green Chem.* 2009, 11, 2034-2040;

Maeda, Y.; Kakiuchi, N.; Matsumura, S.; Nishimura, T.; Kawamura, T.; Uemura, S. *J. Org. Chem.* 2002, 67, 6718-6724;

Maeda, Y.; Kakiuchi, N.; Matsumura, S.; Nishimura, T.; Uemura, S. *Tetrahedron Lett.* 2001, 42, 8877-8879;

Jiang, N.; Ragauskas, A. J. *Tetrahedron Lett.* 2007, 48, 273-276; (b) Jiang, N.;

Ragauskas, A. J. *J. Org. Chem.* 2007, 72, 7030-7033;

Radosevich, A. T.; Musich, C.; Toste, F. D. *J. Am. Chem. Soc.* 2005, 127, 1090-1091;

Pawar, V. D.; Bettigeri, S.; Weng, S. S.; Kao, J. Q.; Chen, C. T. *J. Am. Chem. Soc.* 2006, 128, 6308-6309;

Weng, S. S.; Shen, M. W.; Kao, J. Q.; Munot, Y. S.; Chen, C. T. *Proc. Nat. Acad. Sci.* 2006, 103, 3522-3527;

Ohde, C.; Limberg, C. *Chem. Eur. J.* 2010, 16, 6892-6899;

Hanson, S. K.; Baker, R. T.; Gordon, J. C.; Scott, B. L.; Silks, L. A.; Thorn, D. L. *J. Am. Chem. Soc.* 2010, 132, 17804-17816;

Thorn, D. L.; Harlow, R. L.; Herron, N. *Inorg. Chem.* 1996, 35, 547-548;

Nica, S.; Pohlmann, A.; Plass, W. *Eur. J. Inorg. Chem.* 2005, 2032-2036;

Caravan, P.; Gelmini, L.; Glover, N.; Herring, F. G.; Li, H.; McNeill, J. H.; Rettig, S. J.; Setyawati, I. A.; Shuter, E.; Sun, Y.; Tracey, A. S.; Yuen, V. G.; Orvig, C. *J. Am. Chem. Soc.* 1995, 117, 12759-12770;

Sun, Y.; James, B. R.; Rettig, S. J.; Orvig, C. *Inorg. Chem.* 1996, 35, 1667-1673.

Scheidt, W. R. *Inorg. Chem.* 1973, 12, 1758-1761;

Giacomelli, A.; Floriani, C.; Duarte, A. O. D. S.; Chiesi-Villa, A.; Guastini, C. *Inorg. Chem.* 1982, 21, 3310-3316; (b) Pasquali, M.; Landi, A.; Floriani, C. *Inorg. Chem.* 1979, 18, 2397-2400;

Riechel, T. L.; Sawyer, D. T. *Inorg. Chem.* 1975, 14, 1869-1875; (b) Amos, L. W.;

Sawyer, D. T. *Inorg. Chem.* 1974, 13, 78-83;

Thorn, D. L.; Harlow, R. L.; Herron, N. *Inorg. Chem.* 1996, 35, 547-548;

Hanson, S. K.; Baker, R. T.; Gordon, J. C.; Scott, B. L.; Silks, L. A.; Thorn, D. L. *J. Am. Chem. Soc.* 2010, 132, 17804-17816;

Giacomelli, A.; Floriani, C.; Duarte, A. O. D. S.; Chiesi-Villa, A.; Guastini, C. *Inorg. Chem.* 1982, 21, 3310-3316;

Nica, S.; Buchholz, A.; Rudoph, M.; Schweitzer, A.; Wachtler, M.; Breitzke, H.; Buntkowsky, G.; Plass, W. *Eur. J. Inorg. Chem.* 2008, 2350-2359;

Caravan, P.; Gelmini, L.; Glover, N.; Herring, F. G.; Li, H.; McNeill, J. H.; Rettig, S. J.; Setyawati, I. A.; Shuter, E.; Sun, Y.; Tracey, A. S.; Yuen, V. G.; Orvig, C. *J. Am. Chem. Soc.* 1995, 117, 12759-12770;

Scheidt, W. R. *Inorg. Chem.* 1973, 12, 1758-1761; and

Pasquali, M.; Landi, A.; Floriani, C. *Inorg. Chem.* 1979, 18, 2397-2400.

The invention is illustrated by the following examples which are not intended to be limiting in nature.

A. Experimental Procedures

General Considerations.

Unless specified otherwise, all vanadium complexes were prepared under a dry argon atmosphere using standard glovebox and Schlenk techniques. $CDCl_3$, 1,2-dichloroethane-$d_4$, $CD_2Cl_2$, pyridine-$d_5$, and DMSO-$d_6$ were purchased from Cambridge Isotope Laboratories, and $CD_2Cl_2$ was dried over $CaH_2$. Anhydrous grade acetonitrile, $CH_2Cl_2$, THF, 1,2-dichloroethane, and diethyl ether were obtained from Fisher Scientific and used as received. $^1H$, $^{13}C$, and $^{51}V$ NMR spectra were obtained at room temperature on a Bruker AV400 MHz spectrometer, with chemical shifts (δ) referenced to the residual solvent signal or referenced externally to $V^V(O)(Cl)_3$ (0 ppm). IR spectra were obtained on a Varian 1000 FT-IR Scimitar Series instrument. GC-MS analysis was obtained using a Hewlett Packard 6890 GC system equipped with a Hewlett Packard 5973 mass selective detector. Complexes (dipic)$V^V$(O)(O$^i$Pr) (3) (Thorn, D. L.; Harlow, R. L.; Herron, N. *Inorg. Chem.* 1996, 35, 547-548), (HQC)$V^V$(O)(O$^i$Pr) (4) (Hanson, S. K.; Baker, R. T.; Gordon, J. C.; Scott, B. L.; Silks, L. A.; Thorn, D. L. *J. Am. Chem. Soc.* 2010, 132, 17804-17816), (SAL)$V^V$(O)(O$^i$Pr)(5) (Thorn, D. L.; Harlow, R. L.; Herron, N. *Inorg. Chem.* 1996, 35, 547-548), [(HQ)$_2V^V$(O)]$_2$μ-O (12) (Giacomelli, A.; Floriani, C.; Duarte, A. O. D. S.; Chiesi-Villa, A.; Guastini, C. *Inorg. Chem.* 1982, 21, 3310-3316), and 4-hydroxy-N'-salicylidene-butanohydrazine ($H_2$SALhyhb) (Nica, S.; Buchholz, A.; Rudoph, M.; Schweitzer, A.; Wachtler, M.; Breitzke, H.; Buntkowsky, G.; Plass, W. *Eur. J. Inorg. Chem.* 2008, 2350-2359) were prepared using published procedures. Elemental Analyses were performed by Atlantic Microlab in Norcross, Ga. High resolution mass spectra (HRMS) were obtained by the Laboratory for Biology Mass Spectrometry at Texas A&M University in College Station, Tex.

Synthesis of (SALhyhb)$V^V$(O)(O$^i$Pr) (6)

The ligand 4-hydroxy-N'-salicylidene-butanohydrazine ($H_2$SALhyhb) (470 mg, 2.12 mmol) was suspended in isopropanol (5 mL). $V^V$(O)(O$^i$PR)$_3$ (522 mg, 2.14 mmol) was added, yielding a dark red solution. Within 5 minutes, a redbrown precipitate began to form. Diethylether (10 mL) was added, and the suspension cooled to −20° C. overnight. The supernatant was decanted, and the red-brown solid washed with diethyl ether (10 mL) and dried under vacuum. Yield: 641 mg (87%). $^1$H NMR (400 MHz, $CD_3OD$): δ 8.59 (s, 1H, C=NH), 7.59 (d, 1H, J=7.6 Hz, SAL), 7.53 (t, 1H, J=7.6 Hz, SAL), 7.01 (t, 1H, J=7.2 Hz, SAL), 6.94 (d, 1H, J=8.4 Hz, SAL), 3.95 (h, 1H, J=6.0 Hz, isopropanol), 3.69 (t, 2H, J=6.8 Hz, $CH_2$OH), 2.54 (t, 2H, J=7.2 Hz, N—$CH_2$), 1.98 (quintet, 2H, J=6.8 Hz, —$CH_2$), 1.17 (d, 6H, J=6.0 Hz, isopropanol). $^{13}C\{^1H\}$ NMR (100 MHz, $CD_3OD$): 179.9, 165.3, 153.4, 135.5, 133.8, 121.6, 121.5, 117.9, 64.9, 62.6, 30.6, 29.1, 25.4. $^{51}$V NMR (105 MHz, $CD_3OD$): −549 (s). IR ($CH_2Cl_2$): $v_{C=N}$=1613 cm$^{-1}$, 1558 cm$^{-1}$, $v_{V=O}$=948 cm$^{-1}$. Anal. Calcd for $C_{14}H_{19}N_2O_5V$: C, 48.56; H, 5.53; N, 8.09. Found: C, 48.69; H, 5.48; N, 7.99.

Synthesis of (malt)$_2V^V$(O)(O$^i$Pr) (7)

Complex 7 has been reported previously (Caravan, P.; Gelmini, L.; Glover, N.; Herring, F. G.; Li, H.; McNeill, J. H.; Rettig, S. J.; Setyawati, I. A.; Shuter, E.; Sun, Y.; Tracey, A. S.; Yuen, V. G.; Orvig, C. *J. Am. Chem. Soc.* 1995, 117, 12759-12770). Maltol (1.199 g, 9.516 mmol) was suspended in $CH_3$CN (10 mL). $V^V$(O)(O$^i$Pr)$_3$ (1.161 g, 4.758 mmol) was added, yielding a dark red reaction mixture, which was stirred at room temperature 5 minutes. Upon cooling the mixture to −20° C. overnight, dark red needles formed. The supernatant was decanted, and the crystals washed with diethyl ether (2×3 mL) and dried under vacuum. Yield: 1.766 g (98%). $^1$H NMR (400 MHz, CD$_2$Cl$_2$): δ 7.85 (br s, 2H, malt), 6.45 (br s, 2H, malt), 6.30 (h, 1H, J=6.0 Hz, V—OCH), 2.47 (s, 6H, malt), 1.42 (br s, 6H, V-isopropoxide). $^{13}$C{$^1$H} NMR (100 MHz, CD$_2$Cl$_2$): 174.8 (br), 155.5, 150.6 (br), 110.9 (br), 92.2, 24.8, 14.9. $^{51}$V NMR (105 MHz, CD$_2$Cl$_2$): −433 (s). IR (thin film): $v_{V=O}$=967 cm$^{-1}$. $^1$H NMR data in CDCl$_3$ matched those reported for 7 (Caravan, P.; Gelmini, L.; Glover, N.; Herring, F. G.; Li, H.; McNeill, J. H.; Rettig, S. J.; Setyawati, I. A.; Shuter, E.; Sun, Y.; Tracey, A. S.; Yuen, V. G.; Orvig, C. *J. Am. Chem. Soc.* 1995, 117, 12759-12770). Anal. Calcd for C$_{15}$H$_{17}$O$_8$V: C, 47.89; H, 4.55. Found: C, 48.06; H, 4.48.

Synthesis of (HQ)$_2$V$^V$(O)(O$^i$Pr) (8)

Complex 8 has been reported previously (Giacomelli, A.; Floriani, C.; Duarte, A. O. D. S.; Chiesi-Villa, A.; Guastini, C. *Inorg. Chem.* 1982, 21, 3310-3316 and Scheidt, W. R. *Inorg. Chem.* 1973, 12, 1758-1761). Under air in a 20 mL vial, V$^{IV}$(O)(acac)$_2$ (182 mg, 0.687 mmol) and 8-hydroxyquinoline (199 mg, 1.37 mmol) were suspended in isopropanol (10 mL). The suspension was stirred for 24 hours under air, resulting in a dark red-purple suspension. The dark red solid was collected on a frit under air, washed with isopropanol (2×1 mL), and allowed to dry completely in the air. Yield: 247 mg (87%). $^1$H NMR (400 MHz, CD$_2$Cl$_2$): δ 8.56 (br s, 1H, HQ), 8.41 (br s, 1H, HQ), 8.13 (d, 1H, J=8.0 Hz, HQ), 8.05 (d, 1H, J=8.0 Hz, HQ), 7.58-7.53 (m, 2H, HQ), 7.24-7.13 (m, 6H, HQ), 6.25 (h, 1H, J=6.0, V—OCH), 1.44 (d, 3H, J=6.4 Hz, V-isopropoxide), 1.40 (d, 3H, J=6.0 Hz, V-isopropoxide). $^{13}$C{$^1$H} NMR (100 MHz, CD$_2$Cl$_2$): 164.9, 163.8, 146.3, 145.9, 141.7, 140.0, 138.7, 137.7, 130.4, 129.8, 129.4, 122.6, 122.4, 117.6, 115.2, 111.7, 110.4, 91.2, 25.3, 24.9. $^{51}$V NMR (105 MHz, CD$_2$Cl$_2$): −492 (s). IR (thin film): $v_{V=O}$=957 cm$^{-1}$. Anal. Calcd for C$_{21}$H$_{19}$N$_2$O$_4$V: C, 60.88; H, 4.62; N, 6.76. Found: C, 60.00; H, 4.51; N, 6.56.

Alternate Synthesis of 8.

In a 20 mL vial, V$^V$(O)(O$^i$Pr)$_3$ (1.027 g, 4.209 mmol) was added to a suspension of 8-hydroxyquinoline (1.222 g, 8.428 mmol) in CH$_3$CN (15 mL). The mixture was stirred at room temperature for 4 hours, and then the resulting dark red solid collected on a frit, washed with diethyl ether (3×3 mL), and dried under vacuum. Yield: 1.585 g (91%).

Synthesis of (HQ)$_2$V$^V$(O)(OC$_6$H$_4$OCH$_3$) (9)

Complex (HQ)$_2$V$^V$(O)(O$^i$Pr)(8) (95.6 mg, 0.231 mmol) and 4-methoxybenzylalcohol (440 mg, 3.19 mmol) were suspended in CH$_3$CN (5 mL). The mixture was allowed to stand at room temperature for 4 days, during which time dark red crystals formed. The supernatant was decanted, and the crystals washed with diethyl ether (2×4 mL) and dried under vacuum. Yield: 109 mg (96%). $^1$H NMR (400 MHz, CD$_2$Cl$_2$): δ 8.58 (br s, 1H, HQ), 8.41 (br s, 1H, HQ), 8.14 (d, 1H, J=8.0 Hz, HQ), 8.05 (d, 1H, J=7.2 Hz, HQ), 7.59-7.52 (m, 2H, HQ), 7.29 (d, 2H, J=8.4 Hz, aryl), 7.28-7.12 (m, 6H, HQ), 6.80 (d, 2H, J=8.4 Hz, aryl), 6.72 (d, 1H, J=12.8, V—OCH), 6.57 (d, 1H, J=12.8 Hz, V—OCH), 3.76 (s, 3H, OCH$_3$). $^{13}$C{$^1$H} NMR (100 MHz, CD$_2$Cl$_2$): 163.9, 162.6, 158.8, 145.6, 145.2, 140.8, 139.0, 138.0, 136.9, 132.9, 129.6, 129.5, 128.8, 128.4, 128.3, 121.7, 121.5, 117.2, 114.4, 113.4, 113.1, 110.8, 109.5, 89.2, 54.8. $^{51}$V NMR (105 MHz, CD$_2$Cl$_2$): −473 (s). IR (thin film): $v_{V=O}$=959 cm$^{-1}$. Anal. Calcd for C$_{26}$H$_{21}$N$_2$O$_5$V: C, 63.42; H, 4.30; N, 5.69. Found: C, 62.84; H, 4.33; N, 5.55. HRMS (EI): m/z calcd for C$_{26}$H$_{22}$N$_2$O$_5$V [M+H]$^+$: 473.1079. found: 473.1065.

Reaction of 9 with NEt$_3$ Under Argon.

In a resealable Teflon-capped NMR tube, complex 9 (5.2 mg, 0.011 mmol) was dissolved in CD$_2$Cl$_2$ (0.6 mL) containing diethyl ether (0.023 M) as an internal standard. An initial $^1$H NMR spectrum was recorded, and then NEt$_3$ (3.0 μL, 0.022 mmol) was added. After 2 h at room temperature, integration of the $^1$H NMR spectrum revealed complete consumption of 9, and formation of 4-methoxybenzaldehyde (0.5 equiv, 100%) and 4-methoxybenzylalcohol (0.5 equiv, 100%). Carrying out the reaction on a larger scale using 9 (28.5 mg, 0.0579 mmol) and NEt$_3$ (16 μL, 0.12 mmol) in CH$_2$Cl$_2$ (1.5 mL), allowed for isolation of the vanadium(IV) product as a yellow-brown precipitate (Yield: 19.5 mg, 94%). The IR spectrum of the precipitate was consistent with (HQ)$_2$V$^{IV}$(O) (10), matching that of an authentic sample prepared as described below. When a similar experiment was carried out with complex 9 dissolved in CD$_2$Cl$_2$ and no NEt$_3$ was added, less than 5% of the complex reacted after 16 h at room temperature.

Reaction of 9 with NEt$_3$ Under Air.

In a resealable Teflon-capped NMR tube, complex 9 (3.6 mg, 7.3 μmol) was dissolved in CD$_2$Cl$_2$ (0.6 mL) containing CH$_3$CN (0.026 M) as an internal standard. An initial spectrum was recorded. The tube was opened to air, and NEt$_3$ (2.0 μL, 0.014 mmol) was added. After 22 hours at room temperature, examination of the $^1$H NMR spectrum revealed complete consumption of the starting material and quantitative conversion to (HQ)$_2$V$^V$(O)$_2$HNEt$_3$ (11) and 4-methoxybenzaldehyde. The identity of 11 was verified by independent synthesis as described below.

Synthesis of (HQ)$_2$V$^{IV}$(O) (10)

Complex 10 has been reported previously, and was prepared according to a modified version of a published procedure (Pasquali, M.; Landi, A.; Floriani, C. *Inorg. Chem.* 1979, 18, 2397-2400). In a vial, V$^{IV}$(O)(acac)$_2$ (155 mg, 0.583 mmol) and 8-hydroxyquinoline (174 mg, 1.20 mmol) were suspended in acetone. The reaction mixture was stirred at room temperature overnight, affording a yellow suspension. The yellow solid was collected on a frit, washed with diethyl ether (1×1 mL) and dried under vacuum. Yield: 198 mg (96%). The IR spectrum of the product matched reported data for 10 (Pasquali, M.; Landi, A.; Floriani, C. *Inorg. Chem.* 1979, 18, 2397-2400).

Synthesis of (HQ)$_2$V$^V$(O)$_2$HNEt$_3$ (11)

Under air, the μ-oxo complex [(HQ)$_2$V$^V$(O)]$_2$μ-O (12) (108 mg, 0.147 mmol) was suspended in CH$_2$Cl$_2$ (8 mL). Water (26.5 μL, 1.47 mmol) and NEt$_3$ (205 μL, 1.47 mmol) were added, and the mixture stirred overnight at room temperature, during which time the reaction mixture changed from a gray suspension to a yellow solution. The solvent was removed under vacuum, leaving a yellow-tan solid. The solid was washed with diethyl ether (1×4 mL) and dried under vacuum. Yield: 107 mg (76%). The product was somewhat unstable in the absence of NEt$_3$; a similar loss of amine was reported for the n-butylammonium analogue (Giacomelli, A.; Floriani, C.; Duarte, A. O. D. S.; Chiesi-Villa, A.; Guastini, C. *Inorg. Chem.* 1982, 21, 3310-3316). $^1$H and $^{51}$V NMR spectra were recorded in the presence of added NEt$_3$ (2 equiv). $^1$H NMR (400 MHz, CD$_2$Cl$_2$): δ 8.44 (d, 2H, J=3.6 Hz, HQ), 7.99 (d, 2H, J=8.0 Hz, HQ), 7.45 (t, 2H, J=8.0 Hz, HQ), 7.12 (dd, 2H, J=8.0 Hz, J=3.6 Hz, HQ), 7.02 (dd, 2H, J=7.6 Hz, J=2.8 Hz, HQ), 2.70 (q, 24H, J=6.8 Hz, NEt$_3$), 1.09 (t, 36H, J=6.8 Hz, NEt$_3$). $^{13}$C{$^1$H} NMR (100 MHz, CD$_2$Cl$_2$): 165.7, 144.5, 141.6, 136.8, 130.4, 129.7, 121.9, 113.0, 111.6, 46.9, 12.1. $^{51}$V NMR (105 MHz, CD$_2$Cl$_2$): −526 (s). IR (thin film): $v_{V=O}$=853 cm$^{-1}$, 908 cm$^{-1}$. Anal. Calcd for C$_{24}$H$_{28}$N$_3$O$_4$V: C, 60.89; H, 5.96; N, 8.88. Found: C, 60.07; H, 5.98; N, 8.67. HRMS (EI): m/z calcd for C$_{18}$H$_{12}$N$_2$O$_4$V [M]$^-$: 370.0269. found: 370.0256.

General Procedure for the Catalytic Oxidation.

In a 50 mL roundbottom flask, the substrate (1.0 mmol) was combined with complex 8 (8.3 mg, 0.020 mmol) and NEt$_3$ (14 µL, 0.10 mmol). The mixture was dissolved in 1,2-dichloroethane (2 mL) under air, and the flask equipped with a stir bar and an air condenser. The flask was heated with stirring in an oil bath at 60° C. for 24 h under air. To isolate the product, the solvent was removed under vacuum, and the dark residue was extracted with ethyl acetate/hexanes (3:7), filtered through a plug of silica gel, and the solvent removed under vacuum.

Unless noted otherwise, the general procedure was followed to isolate the products below:

benzaldehyde (92% yield). $^1$H NMR (400 MHz, CDCl$_3$): δ 10.03 (s, 1H), 7.90 (d, 2H, J=7.6 Hz), 7.65 (t, 1H, J=7.6 Hz), 7.55 (t, 2H, J=7.6 Hz). $^{13}$C{$^1$H} NMR (100 MHz, CDCl$_3$): δ 192.6, 136.6, 134.7, 130.0, 129.2.

4-methoxybenzaldehyde (96% yield). $^1$H NMR (400 MHz, CDCl$_3$): δ 9.90 (s, 1H), 7.85 (d, 2H, J=8.8 Hz), 7.02 (d, 2H, J=8.8 Hz), 3.90 (s, 3H). $^{13}$C{$^1$H} NMR (100 MHz, CDCl$_3$): δ 191.1, 164.8, 132.2, 130.1, 114.5, 55.8.

4-nitrobenzaldehyde (96% yield). $^1$H NMR (400 MHz, CDCl$_3$): δ 10.16 (s, 1H), 8.39 (d, 2H, J=8.0 Hz), 8.08 (d, 2H, J=8.0 Hz). $^{13}$C{$^1$H} NMR (100 MHz, CDCl$_3$): δ 190.5, 151.3, 140.2, 130.7, 124.5.

benzophenone (93% yield). The reaction was heated at 60° C. for 72 h. $^1$H NMR (400 MHz, CDCl$_3$): δ 7.82 (d, 4H, J=8.0 Hz), 7.60 (t, 2H, J=8.0 Hz), 7.50 (t, 4H, J=8.0 Hz). $^{13}$C{$^1$H} NMR (100 MHz, CDCl$_3$): δ 197.0, 137.8, 132.6, 130.3, 128.5.

acetophenone (95% yield). The reaction was heated at 80° C. for 24 h using 1 equiv of NEt$_3$. $^1$H NMR (400 MHz, CDCl$_3$): δ 7.96 (d, 2H, J=7.2 Hz), 7.56 (t, 1H, J=7.2 Hz), 7.46 (t, 2H, J=8.0 Hz), 2.61 (t, 3H). $^{13}$C{$^1$H} NMR (100 MHz, CDCl$_3$): δ 198.3, 137.3, 133.3, 128.7, 128.5, 26.8.

cyclopropylphenylketone (90% yield). The reaction was heated at 80° C. for 48 h. $^1$H NMR (400 MHz, CDCl$_3$): δ 8.03 (d, 2H, J=8.0 Hz), 7.58 (t, 1H, J=7.6 Hz), 7.49 (t, 2H, J=7.6 Hz), 2.69 (m, 1H), 1.26 (m, 2H), 1.05 (m, 2H). $^{13}$C{$^1$H} NMR (100 MHz, CDCl$_3$): δ 200.9, 138.2, 132.9, 128.7, 128.2, 17.3, 11.8.

cinnamyl aldehyde (98% yield). $^1$H NMR (400 MHz, CDCl$_3$): δ 9.72 (d, 1H, J=7.2 Hz), 7.60-7.57 (m, 2H), 7.49 (d, 1H, J=16.0 Hz), 7.46-7.44 (m, 3H), 6.74 (dd, 1H, J=16.0 Hz, J=7.6 Hz). $^{13}$C{$^1$H} NMR (100 MHz, CDCl$_3$): δ 194.0, 153.0, 134.2, 131.5, 129.3, 128.8, 128.7.

3-methyl-2-cyclohexen-1-one (96% yield). The reaction was heated at 80° C. $^1$H NMR (400 MHz, CDCl$_3$): 5.88 (m, 1H), 2.34 (t, 2H, J=6.8 Hz), 2.28 (t, 2H, J=6.4 Hz), 1.99 (p, 2H, J=6.4 Hz), 1.96 (s, 3H). $^{13}$C{$^1$H} NMR (100 MHz, CDCl$_3$): δ 200.0, 162.9, 126.9, 37.2, 31.1, 24.6, 22.7.

pyridine-2-carbaldehyde (96% yield). The reaction was heated at 80° C. $^1$H NMR (400 MHz, CDCl$_3$): δ 10.08 (s, 1H), 8.79 (d, 1H, J=4.8 Hz), 7.97 (d, 2H, J=7.6 Hz), 7.88 (t, 1H, J=7.6 Hz), 7.54-7.51 (m, 1H). $^{13}$C{$^1$H} NMR (100 MHz, CDCl$_3$): δ 193.6, 153.0, 150.4, 137.3, 128.1, 121.9.

2,5-diformylfuran (93% yield). $^1$H NMR (400 MHz, CDCl$_3$): δ 9.87 (s, 2H), 7.34 (s, 2H). $^{13}$C{$^1$H} NMR (100 MHz, CDCl$_3$): δ 179.4, 154.4, 119.4.

2-allyloxybenzaldehyde (95% yield). $^1$H NMR (400 MHz, CDCl$_3$): δ 10.54 (s, 1H), 7.84 (dd, 1H, J=7.6 Hz, J=1.6 Hz, aryl), 7.55 (dd, 1H, J=8.4 Hz, J=1.6 Hz, aryl), 7.03 (t, 1H, J=7.6 Hz, aryl), 6.98 (d, 1H, J=8.4 Hz, aryl), 6.07 (m, 1H, OCH$_2$CH=CH$_2$), 5.46 (d, 1H, J=16.8 Hz, OCH$_2$CH=CHH), 5.34 (d, 1H, J=10.8 Hz, OCH$_2$CH=CHH), 4.66 (d, 2H, J=5.2 Hz, OCH$_2$CH=CH$_2$). $^{13}$C{$^1$H} NMR (100 MHz, CDCl$_3$): δ 189.9, 161.1, 136.0, 132.5, 128.6, 125.2, 121.0, 118.2, 113.0, 69.3.

4-phenyl-3-butyn-2-one (96% yield). The reaction was heated at 80° C. $^1$H NMR (400 MHz, CDCl$_3$): δ 7.58-7.57 (m, 2H), 7.47-7.43 (m, 1H), 7.40-7.36 (m, 2H), 2.45 (s, 3H). $^{13}$C NMR (100 MHz, CDCl$_3$): δ 184.8, 133.2, 130.9, 128.8, 120.0, 90.5, 88.4, 32.9.

General Procedure for Testing Catalysts.

In a 50 mL roundbottom flask, 4-methoxybenzylalcohol (70 mg, 0.50 mmol), the appropriate vanadium complex (0.01 mmol), NEt$_3$ (7 µL, 0.05 mmol) and a 1,3,5-tri-tert-butylbenzene internal standard (ca. 10 mg, 0.04 mmol) were dissolved in 1,2-dichloroethane (1 mL) under air. The flask was equipped with a stir bar and an air condenser. The flask was heated with stirring under air for 24 h at 60° C., then cooled to room temperature and the solvent removed under vacuum. The residue was dissolved in CDCl$_3$ (0.6 mL), and the yield of 4-methoxybenzaldehyde determined by integration of the $^1$H NMR spectrum against the internal standard.

General Procedure for Testing Solvents.

In a 50 mL roundbottom flask, 4-methoxybenzylalcohol (70 mg, 0.50 mmol), complex 8 (4.2 mg, 0.010 mmol), NEt$_3$ (7 µL, 0.05 mmol), and a 1,3,5-tri-tert-butylbenzene internal standard (ca. 5 mg, 0.02 mmol) were dissolved in the appropriate solvent (1 mL). The flask was equipped with a stir bar and an air condenser, and the mixture was heated at 60° C. for 24 hours under air with stirring. The reaction mixture was cooled to room temperature and the solvent removed under vacuum. The residue was dissolved in CDCl$_3$ and the yield of 4-methoxybenzaldehyde determined by integration of the $^1$H NMR spectrum against the internal standard. To determine the reaction yield in pyridine and DMSO solvents, analogous catalytic reactions were carried out in pyridine-d$_5$ and DMSO-d$_6$ solvent and the yield determined by integration of the $^1$H NMR spectrum.

General Procedure for Solvent-Free Catalytic Oxidation.

In a 25 mL roundbottom flask, the substrate (2.0 mmol) was combined with complex 8 (17 mg, 0.040 mmol) and NEt$_3$ (28 µL, 0.20 mmol). The flask was equipped with an air condenser and a stir bar and the reaction mixture was heated at 100° C. for 24 h. After cooling to room temperature, the residue was extracted with ethyl acetate/hexanes (3:7), filtered through a plug of silica gel, and the solvent removed under vacuum. This procedure afforded high yields of benzaldehyde (95%), 4-methoxybenzaldehyde (96%), acetophenone (92%), benzophenone (99%), cyclopropylphenylketone (89%), and isopropylphenylketone (95%). Although benzaldehyde and 4-methoxybenzaldehyde were isolated selectively immediately following the reaction, further oxidation to the corresponding benzoic acid was observed when the isolated product stood for several days at room temperature. This solvent-free procedure was not generally extended to the allylic and propargylic alcohols, as lower selectivity was observed in the oxidation of 3-methyl-2-cyclohexen-1-ol, which afforded 3-methyl-2-cyclohexen-1-one in 74% yield.

Lower selectivity was also observed when cinnamyl alcohol and 4-phenyl-3-butyn-2-ol were oxidized following this procedure.

General Procedure for Testing Additives.

In a 50 mL roundbottom flask, 4-methoxybenzylalcohol (70 mg, 0.50 mmol), complex 8 (4.2 mg, 0.010 mmol), the appropriate additive (0.05 mmol), and a 1,3,5-tri-tert-butylbenzene internal standard (ca. 6 mg, 0.02 mmol) were dissolved in 1,2-dichloroethane (1 mL). The flask was equipped with a stir bar and an air condenser and the mixture was heated at 60° C. for 24 hours under air with stirring. The reaction mixture was cooled to room temperature and the solvent removed under vacuum. The residue was dissolved in $CDCl_3$ and the yield of 4-methoxybenzaldehyde determined by integration of the $^1H$ NMR spectrum against the internal standard.

Catalytic Oxidation of 2-Allyloxybenzyl Alcohol (10 Mmol Scale).

In a 500 mL roundbottom flask, 2-allyloxybenzyl alcohol (1.640 g, 10.00 mmol), complex 8 (0.0823 g, 0.199 mmol), and triethylamine (140 μL, 1.01 mmol) were dissolved in 1,2-dichloroethane (20 mL). The flask was equipped with a stir bar and an air condenser and heated at 60° C. for 24 h. At this time, TLC of the reaction mixture indicated that the reaction was not yet complete. The flask was heated for an additional 14 h under air, and then cooled to room temperature. The solvent was removed under vacuum, and the dark liquid eluted through silica gel using ethyl acetate/hexanes (3:7). Yield: 1.517 g (94%). A minor product identified as 2-allyloxycinnamyl aldehyde was also detected by $^1H$ NMR in approximately 2-4% yield; this product was isolated for characterization by prep-scale TLC chromatography on silica gel using 9:1 hexanes:ethyl acetate. $^1H$ NMR for 2-allyloxycinnamyl aldehyde (400 MHz, $CDCl_3$) δ 9.71 (d, 1H, J=8.0 Hz, HC=O), 7.89 (d, 1H, J=16.4 Hz, aryl-CH=CH), 7.58 (dd, 1H, J=7.6, 1.6 Hz, aryl), 7.40 (dt, 1H, J=7.6, 1.6 Hz, aryl), 7.02 (t, 1H, J=7.6 Hz, aryl), 6.95 (d, 1H, J=8.0 Hz, aryl), 6.81 (dd, 1H, J=16.4, 8.0 Hz, aryl-CH=CHCHO), 6.11 (m, 1H, $OCH_2CH=CH_2$), 5.45 (d, 1H, J=17.2 Hz, $OCH_2CH=CHH$), 5.35 (d, 1H, J=10.4 Hz, $OCH_2CH=CHH$), 4.66 (d, 2H, J=5.6 Hz, $OCH_2CH=CH_2$). $^{13}C\{^1H\}$ NMR (100 MHz, $CDCl_3$): δ 194.8, 157.5, 148.3, 132.9, 132.8, 129.3, 129.1, 123.5, 121.3, 118.4, 112.8, 69.5. MS (EI) m/z: 188 ($M^+$), 147, 131, 118, 103, 91.

Catalytic Oxidation of 3-phenyl-2-propyn-1-ol.

Complex 8 (4.1 mg, 0.010 mmol), $NEt_3$ (7 μL, 0.05 mmol), 3-phenyl-2-propyn-1-ol (69 mg, 0.52 mmol), and a 1,3,5-tri-tert-butylbenzene internal standard (13 mg, 0.051 mmol) were dissolved in 1,2-dichloroethane-$d_4$ (1 mL). An initial $^1H$ NMR spectrum was recorded, and then the reaction mixture heated at 60° C. for 24 h under air with stirring in a 100 mL roundbottom flask equipped with an air condenser. The reaction mixture was cooled to room temperature, and then the mixture transferred to an NMR tube. Examination of the $^1H$ spectrum revealed the formation of 3-phenyl-2-propyn-1-al in 80% yield. $^1H$ NMR (400 MHz, 1,2-dichloroethane-$d_4$) δ 9.42 (s, 1H), 7.63 (d, 2H, J=7.6 Hz), 7.51 (t, 1H, J=7.6 Hz), 7.43 (t, 2H, J=7.6 Hz). $^{13}C\{^1H\}$ NMR (100 MHz, 1,2-dichloroethane-$d_4$): δ 176.8, 133.4, 131.5, 129.0, 119.6, 94.4, 88.6.

Catalytic Oxidation of 2-decyn-1-ol.

Complex 8 (1.4 mg, 0.0034 mmol), $NEt_3$ (2.4 μL, 0.018 mmol), 2-decyn-1-ol (27 mg, 0.18 mmol) and a 1,3,5-tri-tert-butylbenzene internal standard (9.5 mg, 0.039 mmol) were dissolved in 1,2-dichloroethane-$d_4$ (0.7 mL). An initial $^1H$ NMR spectrum was recorded, and then the mixture heated at 60° C. for 24 h with stirring in a 50 mL roundbottom flask equipped with an air condenser. The mixture was cooled to room temperature and transferred to an NMR tube. $^1H$ and $^{13}C$ NMR spectra indicated the formation of 2-decyn-1-al in 60% yield. $^1H$ NMR (400 MHz, 1,2-dichloroethane-$d_4$) δ 9.16 (s, 1H), 2.42 (t, 2H, J=7.2 Hz), 1.59 (p, 2H, J=7.2 Hz), 1.43-1.30 (m, 8H), 0.90 (t, 3H, J=7.2 Hz). $^{13}C\{^1H\}$ NMR (100 MHz, 1,2-dichloroethane-$d_4$): δ 177.1, 99.0, 81.9, 31.9, 29.0, 28.9, 27.9, 22.8, 19.2, 14.1.

Catalytic Oxidation of 1-phenyl-2-propyn-1-ol.

Complex 8 (2.9 mg, 0.0070 mmol), $NEt_3$ (4.8 μL, 0.035 mmol), 1-phenyl-2-propyn-1-ol (46 mg, 0.35 mmol), and a 1,3,5-tri-tert-butylbenzene internal standard (14 mg, 0.056 mmol) were dissolved in 1,2-dichloroethane-$d_4$. An initial $^1H$ NMR spectrum was recorded, and then the reaction mixture heated at 60° C. for 24 h with stirring in a 50 mL roundbottom flask equipped with an air condenser. The mixture was cooled to room temperature and transferred to an NMR tube. $^1H$ and $^{13}C$ NMR spectra revealed complete consumption of the starting material and the formation of 1-phenyl-2-propyn-1-one in 38% yield. $^1H$ NMR (400 MHz, 1,2-dichloroethane-$d_4$) δ 8.39 (s, 1H), 7.87 (d, 2H, J=7.6 Hz), 7.64 (t, 1H, J=7.6 Hz), 7.54 (t, 2H, J=7.6). $^{13}C\{^1H\}$ NMR (100 MHz, 1,2-dichloroethane-$d_4$): δ 194.6, 138.3, 136.8, 134.1, 133.3, 130.2, 128.8.

Effect of Flask Size on the Catalytic Oxidation of 4-Methoxybenzylalcohol.

A stock solution was prepared by dissolving 4-methoxybenzylalcohol (0.277 g, 2.01 mmol), complex 8 (0.017 g, 0.040 mmol), $NEt_3$ (28 μL, 0.20 mmol), and a 1,3,5-tri-tert-butylbenzene internal standard (0.049 g, 0.20 mmol) in 1,2-dichloroethane (4 mL). The stock solution was split between a 100 mL roundbottom flask (2 mL) and a 10 mL Schlenk tube (2 mL). Each flask was equipped with a stir bar and an air condenser and heated at 60° C. for 4 hours with stirring. The reactions were cooled to room temperature, the solvent removed under vacuum, and the residue dissolved in $CDCl_3$. The extent of conversion was determined by integration against the internal standard; 55% conversion was observed in the wider 100 mL flask, while only 31% conversion was observed in the narrow 10 mL tube.

Effect of Stir Rate on the Catalytic Oxidation of 4-Methoxybenzylalcohol.

A stock solution was prepared by dissolving 4-methoxybenzylalcohol (0.276 g, 2.00 mmol), complex 8 (0.0166 g, 0.0401 mmol), $NEt_3$ (28 μL, 0.20 mmol), and a 1,3,5-tri-tert-butylbenzene internal standard (0.066 g, 0.27 mmol) in 1,2-dichloroethane (4 mL). To each of two 25 mL roundbottom flasks was added 2 mL of the stock solution. The flasks were each equipped with an air condenser and heated at 60° C. using an IKA Werke basic temperature controlled oil bath. The first flask was stirred at ~900 rpm (setting level 8), while the second flask was stirred at ~200 rpm (setting level 2). After 4 hours of heating, the reactions were cooled to room temperature and the solvent removed under vacuum. The residue in each flask was dissolved in $CDCl_3$, and the extent of conversion determined by integration against the internal standard. The flask stirred at ~900 rpm showed 43% conversion, while the flask stirred at ~200 rpm showed only 35% conversion.

Catalytic Oxidation with Added $H_2O$.

Complex 8 (8.8 mg, 0.021 mmol) and $NEt_3$ (14 μL, 0.10 mmol) were dissolved in 1,2-dichloroethane (2 mL). The solution was added to a flask containing 4-methoxybenzyl alcohol (140 mg, 1.01 mmol), $H_2O$ (91 μL, 5.05 mmol), and a 1,3,5-tri-tert-butylbenzene internal standard (19.2 mg, 0.078 mmol). The flask was equipped with an air condenser and a stir bar and heated at 60° C. for 24 h with stirring (~700 rpm). The reaction mixture was cooled to room temperature, the solvent removed under vacuum, and the extent of conversion determined by integration of the $^1$H NMR spectrum against the internal standard. 4-Methoxybenzaldehyde was formed in >98% yield (based on the average of two runs of this type).

Catalytic Oxidation of a Mixture of 4-Methoxybenzyl Alcohol and 1-Octanol.

In a 50 mL roundbottom flask under air, 4-methoxybenzyl alcohol (68.9 mg, 4.99 mmol) and complex 8 (8.3 mg, 0.020 mmol) were dissolved in 1,2-dichloroethane (2 mL). 1-Octanol (79 μL, 5.0 mmol) and triethylamine (14 μL, 0.10 mmol) were added. The flask was equipped with a stir bar and an air condenser, and heated at 60° C. for 24 h with stirring. The reaction mixture was cooled to room temperature and the solvent removed under vacuum. The product mixture was isolated by extraction of the dark residue with a mixture of ethyl acetate and hexanes (3:7), filtration through a plug of silica gel in a pipette, and removal of the solvent under vacuum. Yield: 128 mg (96% material recovery). Examination of the $^1$H and $^{13}$C NMR spectra of the products revealed a mixture of 4-methoxybenzaldehyde and 1-octanol. No 1-octanal was detected.

What is claimed is:

1. A process for oxidizing an alcohol to produce a carbonyl compound, said process comprising contacting the alcohol with
    (i) a gaseous mixture comprising oxygen; and
    (ii) an amine compound;
    said contacting occurring in the presence of a catalyst, said catalyst comprising two nitrogen-containing heterocycles complexed with vanadium and having the formula:

wherein:
each of $R^1$-$R^{12}$ are independently H, alkyl, aryl, $CF_3$, halogen, $OR^{13}$, $SO_3R^{14}$, $C(O)R^{15}$, $CONR^{16}R^{17}$ or $CO_2R^{18}$;
each of $R^{13}$-$R^{18}$ is independently alkyl or aryl; and
Z is alkl or aryl.

2. The method of claim 1, wherein Z is alkyl.
3. The method of claim 1, wherein Z is isopropyl.
4. The method of claim 1, wherein said amine is a trialkyl amine.
5. The method of claim 1, wherein said amine is triethylamine.
6. The method of claim 1, wherein each of $R^1$-$R^{12}$ is H, alkyl or aryl.
7. The method of claim 1, wherein each of $R^1$-$R^{12}$ is H.
8. The method of claim 7, wherein Z is isopropyl.
9. The method of claim 8, wherein said amine is triethylamine, diisopropylethylamine, 1,4-diazabicyclo[2.2.2]octane, or 2,2,6,6-tetramethylpiperidine-1-oxyl.
10. The method of claim 8, wherein said amine is triethylamine.
11. The method of claim 1, wherein said alcohol is of the formula wherein $R^{19}$ is selected from aryl, vinyl, and alkynyl, and wherein $R^{20}$ is selected from H, methyl, and aryl.

12. The method of claim 9, wherein said alcohol is of the formula wherein $R^{19}$ is selected from aryl, vinyl, and alkynyl, and wherein $R^{20}$ is selected from H, methyl, and aryl.

13. The method of claim 1, wherein said contacting occurs in the presence of a solvent selected from one or more of water, 1,2-dichloroethane, ethylacetate, toluene, tetrahydrofuran, acetonitrile, dichloromethane, 1,2-dichlorobenzene and 2-methyl-tetrahydrofuran.
14. The method of claim 1, wherein said alcohol is a benzylic alcohol, allylic alcohol, or propargylic alcohol.
15. The method of claim 1, wherein said contacting occurs at a temperature in the range of from 25° C. to 150° C.
16. The method of claim 15, wherein said catalyst is of the formula 17. The method of claim 1, wherein said gaseous mixture is air.

* * * * *